(12) United States Patent
Huber

(10) Patent No.: US 8,043,634 B2
(45) Date of Patent: Oct. 25, 2011

(54) DRUG AND/OR FOOD SUPPLEMENT CONTAINING NISYLEN, CEPA, EUPHRASIA, BELLADONNA AND/OR MERCURIUS SOLUBILIS

(76) Inventor: Klaus Huber, Bad Tolz (DE)

( * ) Notice: Subject to any disclaimer, the term of this patent is extended or adjusted under 35 U.S.C. 154(b) by 50 days.

(21) Appl. No.: 12/345,317

(22) Filed: Dec. 29, 2008

(65) Prior Publication Data

US 2009/0110747 A1 Apr. 30, 2009

Related U.S. Application Data

(62) Division of application No. 11/496,756, filed on Jul. 31, 2006, now abandoned.

(30) Foreign Application Priority Data

Mar. 28, 2006 (DE) .................... 20 2006 006 962 U
Mar. 30, 2006 (EP) .................... 06 006 727

(51) Int. Cl.
*A61K 36/00* (2006.01)
*A61K 36/714* (2006.01)
*A61K 36/81* (2006.01)
*A61K 36/8962* (2006.01)
*A61K 33/42* (2006.01)

(52) U.S. Cl. .................... 424/725; 424/601; 424/754
(58) Field of Classification Search .................... None
See application file for complete search history.

(56) References Cited

U.S. PATENT DOCUMENTS

| | | | |
|---|---|---|---|
| 6,063,383 A | 5/2000 | Hsu et al. | |
| 6,441,273 B1 | 8/2002 | Aldwinckle et al. | |
| 6,455,070 B1 | 9/2002 | Voorhees et al. | |
| 6,641,801 B1 | 11/2003 | Brown | |
| 2002/0025314 A1 | 2/2002 | Etienne | |
| 2004/0156920 A1 | 8/2004 | Kane | |

FOREIGN PATENT DOCUMENTS

| | | |
|---|---|---|
| JP | 362096418 A | 5/1987 |
| RU | 2 006 228 C1 | 1/1994 |
| RU | 2 143 917 C1 | 1/2000 |
| RU | 2174003 C1 | 9/2001 |
| RU | 2218168 C2 | 12/2003 |
| RU | 2 253 472 C1 | 6/2005 |
| WO | WO 8809178 | 12/1988 |
| WO | WO 03059071 | 7/2003 |
| WO | WO 2004035071 | 4/2004 |

OTHER PUBLICATIONS

Ernst 1, is homeopathy a clinically valuable approach? Trends in pharmacological sciences 26 911): 657-548, 2005.*
Kleijnen et al, Clinical trails of homoeopathy, BMJ 302: 316-323, 1991.*
Weissmann, Homeopathy: Holmes, Hogwarts, and the price of Wales, The FASEB Journal 20: 1755-1757, 2006.*
Efficacy of homeopathic Arnica, Arch Surg 133: 1187-1190, 1998.*
Ernst, A systematic review of systematic reviews of homeopathy, Br J Clin Pharmacol 54: 577-582, 2002.*
Bushsel, Report of this year's influenza treated with nisylen. Ther Ggw. Jul. ; 94(7); pp. 264-265, 1995; XP-002417561.
Bluher, Phosphorus and Influenza; a homeopathic Comparison, Hippokrates Verlag Stuttgart; 26 (10); May 31, 1955; pp. 311-312.
European Patent Office, European Search Report of 06011779.3-2107, May 16, 2007, Europe.
ISA European Patent Office, International Search Report of PCT/EP2007/002259, Nov. 16, 2007, WIPO.
Dr. Veronica Carstens, "Homöopathishche complex resources can help" Good natural remedies, edition 2004, 5 Pgs, Machine generated translation (English) 1, Pg.
Dr. Carstens comments.(Carstens, MD Veronica) Tags: cold; Nature and Medicine, 6, 2000, 2 Pgs, Machine generated translation (English) 1 Pg.
"CAM Basics: What Is Complementary and Alternative Medicine?," National Center for Complementary and Alternative Medicine, U.S. Department of Health and Human Services, <http://nccam.nih.gov/health/whatiscam/>, Web page last updated: Nov. 22, 2010, 8 pages.
Huber, Klaus, "The Safety and Efficacy of Use of the homeopathic compound "Herax" as Treatment for Herpes Labialis," Interventional Case Study, May 18, 2008, 7 pages.
Gomeopatiya: Polnaya entsiklopedia [Homeopathy: Complete encyclopedia] Compiled by A.N. Alefirov, St. Petersburg, Vess, 2001 (D3).

* cited by examiner

*Primary Examiner* — Qiuwen Mi
(74) *Attorney, Agent, or Firm* — Alleman Hall McCoy Russell & Tuttle LLP

(57) ABSTRACT

The present disclosure relates to a drug and/or food supplement with antiviral effects, in particular for the preventive and/or therapeutic treatment of herpes labialis and/or herpes genitalis, and/or with antibacterial and/or immunomodulating and/or antiphlogistic effects and/or for the preventive and/or therapeutic treatment of affections of the prostate, containing NISYLEN® and/or Cepa and/or Euphrasia and/or Belladonna and/or Mercurius solubilis.

11 Claims, No Drawings

DRUG AND/OR FOOD SUPPLEMENT CONTAINING NISYLEN, CEPA, EUPHRASIA, BELLADONNA AND/OR MERCURIUS SOLUBILIS

CROSS-REFERENCE TO RELATED APPLICATIONS

This application is a division of U.S. patent application Ser. No. 11/496,756 (now abandoned) filed on Jul. 31, 2008, which claims priority to German Patent Application Serial No. 20 2006 004 962.2 filed Mar. 28, 2006, and also claims priority to European Patent Application Serial No. 06 006 727.9 filed Mar. 30, 2006, each of which are hereby incorporated by reference in their entirety for all purposes.

FIELD

The present disclosure relates to a drug and/or food supplement containing NISYLEN®, Cepa, Euphrasia., Belladonna and/or Mercurius solubilis and to the use of NISYLEN® and/or Cepa and/or Euphrasia and/or Belladonna and/or Mercurius solubilis for a drug and/or food supplement and for the manufacture thereof.

BACKGROUND AND SUMMARY

NISYLEN® is known as a drug for use against influenza infections, fever, sore throat, headache, and cough. It is a homeopathic drug in the form of a compound preparation comprising various active substances, which is available in the form of tablets or a solution for oral administration. The active substances include *Aconitum* Dil. D3, *Gelsemium* Dil. D3, *Ipecacuanha* Dil. D3, Phosphorus Dil. D5, *Bryonia* Dil. D2 and *Eupatorium perfoliatum* Dil. D1. *Aconitum* is an extract of *Actonitum*, which is a flowering plant belonging to the buttercup family. *Gelsemium* is an extract of *Gelsemium*, which is a flowering plant belonging to the family of Gelsemiaceae. *Ipecacuanha* is an extract of *Ipecacuanha*, which is a flowering plant in the family of Rubiaceae, the root of which is most commonly used to make syrup of ipecac, a powerful emetic. Phosphorus is a homeopathic remedy derived from phosphorus, such as potassium phosphate or magnesium phosphate. *Bryonia* is an extract from Bryony, which is a perennial, tendril-climbing flowering plant in the genus of *Bryonia*. *Eupatorium perfoliatum* is an extract of *Eupatorium perfoliatum*, which is a poisonous herbaceous perennial flowering plant.

Homeopathic active ingredients are often diluted with diluents, such as water and alcohol. Dil. 1D indicates that the active ingredient is diluted to $1/10$ of its original strength. Dil 2D indicates that the active ingredient is diluted to $1/100$ of its original strength. Dil 3D indicates that the active ingredient is diluted to $1/1000$ of its original strength, and so forth. As used herein, the dilution of an active ingredient from its original strength is understood to mean the dilution of the active ingredient from its standard mother tincture that is prepared according to standardized guidelines and protocols. Such guidelines may be found in standard homeopathic textbooks or pharmacopoeia, such as the Homeopathic Pharmacopoeia of the United States (HPUS).

What is likewise known is the use of Cepa, Euphrasia, Belladonna and Mercurius solubilis for homeopathic drugs.

It is the object underlying the present disclosure to indicate further medical uses of one or more of the ingredients stated above.

The present disclosure is based on the knowledge that NISYLEN® and/or Cepa and/or Euphrasia and/or Belladonna and/or Mercurius solubilis have antiviral effects, in particular in the preventive and/or therapeutic treatment of herpes labialis and/or herpes genitalis, and/or antibacterial and/or immunomodulating and/or antiphlogistic, i.e. anti-inflammatory effects and/or can be used for the preventive and/or therapeutic treatment of affections of the prostate, in particular for the treatment of prostatitis or of degenerations of the prostate.

Herpes labialis is a viral disease which is caused by the type I herpes simplex virus (HSV Type I), where small, oozing vesicles are formed on the lips, which are sore, cause pain and itching, and are highly infectious. It may also be referred to as a cold sore.

Herpes genitalis is caused by the type II herpes simplex virus (HSV Type II). In the case of herpes genitalis there are also formed vesicles filled with liquid, which cause considerable pain, neuralgias and itching, and are likewise highly infectious.

Both types of virus (HSV Types I and II) affect the skin, mucous membranes, eyes, the nervous system and in rare cases also inner organs. Due to the fact that the virus is constantly present in the body, relapses, i.e. new outbreaks of the disease, can occur again and again. The medicaments known at present are virostatics (which inhibit the growth of the virus but do not necessarily kill the virus), which shorten the course of the disease and alleviate the symptoms.

It has now been found in accordance with the present disclosure that a drug or food supplement which contains NISYLEN® and/or Cepa and/or Euphrasia and/or Belladonna and/or Mercurius solubilis exhibits antiviral effects and can be used for instance for the preventive and therapeutic treatment of herpes. Furthermore, it was found in accordance with the present disclosure that a drug or food supplement which contains NISYLEN® and/or Cepa and/or Euphrasia and/or Belladonna and/or Mercurius solubilis exhibits antibacterial and/or immunomodulating and/or antiphlogistic effects. Furthermore, it was found in accordance with the present disclosure that a drug or food supplement which contains NISYLEN® and/or Cepa and/or Euphrasia and/or Belladonna and/or Mercurius solubilis can be used for the preventive and/or therapeutic treatment of affections of the prostate, such as prostatitis or degenerations of the prostate.

The explanations given below concerning the inventive drug correspondingly apply to the food supplement in accordance with the present disclosure.

The treatment of patients suffering from herpes labialis and of patients suffering from herpes genitalis with the drug in accordance with the present disclosure has shown that the course of the disease has been shortened considerably in both cases. The treatment of patients suffering of affections of the prostate with the inventive drug has shown that not only the PSA value (PSA=prostate-specific antigen), but also the PSA quotient has been improved considerably. The quotient of free PSA and total PSA value as measured in the serum of patients at the time of diagnosis is regarded as a measure for the malignancy of a tumor, the smaller the quotient, the more malignant the tumor.

In accordance with the present disclosure it can be provided that the drug contains one of the active substances NISYLEN® or Cepa or Euphrasia or Belladonna or Mercurius solubilis as main ingredient and one or more of the further ingredients as secondary ingredients, the main ingredient being present in a larger amount or concentration than any of the further ingredients.

It is conceivable in principle that the drug contains only NISYLEN®, only Cepa, only Euphrasia, only Belladonna or only Mercurius solubilis as the active substance.

The present disclosure comprises any combinations of the ingredients mentioned above, for instance a drug comprising NISYLEN® as main ingredient and all the others of said ingredients of the combinations thereof as secondary ingredients.

Preferably, it is provided that the drug contains NISYLEN®.

In accordance with a another aspect it is provided that the drug furthermore contains Cepa. Cepa is an extract from the plant Cepa (or Allium Cepa). Cepa likewise is a homeopathically active substance, which generally is used against a cold.

In accordance with a further aspect of the present disclosure, the drug furthermore contains *Euphrasia*. *Euphrasia* is an extract from the plant Euphrasia, which is herbaceous flowing plant in the family of Orobanchaceae. *Euphrasia* likewise is a substance known from homeopathy, which generally is used against affections of the eyes.

Additional ingredients of the drug in accordance with the present disclosure can be Belladonna and/or Mercurius solubilis. Belladonna is an extract from the plant belladonna, which is a member of the nightshade family. At present, Belladonna is used as a homeopathic medicament against various forms of inflammations. Mercurius solubilis is a homeopathic medicament which is known for the treatment of, for instance, sore throat, otitis media and hoarseness. Mercurius solubilis is the nitrate salt of mercury and can be prepared by dissolving liquid mercury in nitric acid.

In accordance with a further aspect of the present disclosure it is possible that—as far as contained in the drug—the ingredients Cepa, Euphrasia and Mercurius solubilis are present in the dilution D12 and Belladonna in the dilution D15. In principle, it is likewise possible to use the active substances in other dilutions.

It can be particularly advantageous when the ingredient NISYLEN® is present in the drug in a larger amount or concentration than the further ingredients.

Preferably, the drug contains NISYLEN®, Cepa, Euphrasia, Belladonna and Mercurius solubilis, NISYLEN® being present in the drug in a larger amount than the other ingredients mentioned above.

Particularly advantageously, the ingredient NISYLEN® is present in two to four times, preferably three times the amount of any of the further active substances of the drug.

In accordance with a further aspect of the invention it is provided that the drug contains NISYLEN in a weight or in a volume of 4.0 to 4.5 g or ml, preferably in a weight or volume of 4.286 g or ml, and Cepa, Euphrasia, Belladonna and Mercurius solubilis each in a weight or in a volume of 1.2 to 1.6 g or ml, preferably in a weight or in a volume of 1.429 g or ml per 10 ml or 10 g of solution or drug or food supplement.

It is conceivable to prepare the drug for oral administration and/or for topical application. The latter can for instance be relevant in the treatment of herpes labialis.

In accordance with a preferred aspect, the drug is present in liquid form, which can be an alcoholic solution for oral administration. Other solutions than alcohol are conceivable as well. In principle it is likewise conceivable to provide the drug in solid form, for instance as powder, tablets or globuli. It is also possible to provide the drug in pasty form or as an ointment.

The drug preferably is a homeopathic drug.

The ingredient NISYLEN® can contain the following ingredients: *Aconitum napellus*, *Gelsemium sempervirens*, *Cephaelis ipecacuanha*, Phosphorus, *Bryonia* and *Eupatorium perfoliatum*. It is conceivable that per 1 g of NISYLEN® the ingredients are included in the following amounts: 100 mg of *Aconitum napellus* D3, 100 mg of *Gelsemium sempervirens* D3, 100 mg of *Cephaelis ipecacuanha* D3, 100 mg of Phosphorus D5, 100 mg of *Bryonia* D2, and 100 mg of *Eupatorium perfoliatum* D1.

Further details and advantages of the invention will be explained in detail with reference to an embodiment illustrated below. Also, the drug and/or supplement can be packaged with instructions indicating the potential uses or ailments for which it may be taken, such as one or more of those noted herein.

The drug in accordance with the embodiment described here contains the following ingredients:

| | |
|---|---|
| NISYLEN ®: | 4.286 g |
| Cepa D12: | 1.429 g |
| Euphrasia D12: | 1.429 g |
| Belladonna D15: | 1.429 g |
| Mercurius solubilis D12: | 1.429 g |

These ingredients are present in an alcoholic solution in a volume of 10 ml.

As stated above, such a solution is, among other things, excellently suited for the treatment of herpes genitalis and of herpes labialis as well as for the treatment of affections of the prostate.

It can be provided to take for instance 3×5 drops per day in the case of adults and 3×2 drops per day in the case of children. Particularly preferably, the drug should be taken regularly.

In the acute stage, or preferably in the prodromal stage, a half-hourly to hourly application is conceivable as well, i.e. per half an hour to an hour e.g. 5 drops (adults) or 2 drops (children) of the solution should be taken.

It can be advantageous not to dilute the solution and keep it in the mouth as long as possible. It furthermore turns out to be advantageous to drink much, if possible about 3 l/day.

As stated above, the above-mentioned herpes diseases frequently have relapses, which can occur once or several times a year, possibly also every month. The medicaments known so far are helpful in the acute stage by shortening the course of the disease and possibly by alleviating the symptoms, but cannot prevent the occurrence of relapses. In addition, resistances to the known medicaments have meanwhile occurred.

The present disclosure opens up the possibility to achieve an effective treatment of herpes genitalis as well as herpes labialis by means of a particularly effective medicament/food supplement. An effective treatment of affections of the prostate, in particular of prostatitis or degenerations of the prostate, is possible as well.

In principle, deviations from the embodiment of the present disclosure described above in detail are comprised as well. The solvent need not be an alcoholic solvent. In principle, other suitable solvents can be used as well. As stated above, the present disclosure furthermore is not restricted to the application as liquid medicament. It is likewise conceivable to provide the medicament in solid form (tablets, powder, globuli) or as an ointment.

The invention claimed is:

1. A method for,
reducing a course of herpes labialis and/or herpes genitalis compromising administering a with antiviral effects to a patient suffering from herpes labialis and/or herpes genitalis, the medicament comprising *Aconitum napel-* lus diluted to 1/1000 of its standard tincture, *Gelsemium sempervirens* diluted to 1/1000 of its standard tincture, *Cephaelis ipecacuanha* diluted to 1/1000 of its standard tincture, Phosphorus diluted to 1/100000 of its standard tincture, Bryonia diluted to 1/100 of its standard tincture, *Eupatorium perfoliatum* diluted to 1/10 of its standard tincture, cepa Euphrasia, belladonna and Mercurius solubilis.

2. The method of claim 1, wherein in the medicament, a combination including the *Aconitum napellus* diluted to 1/1000 of its standard tincture, the *Gelsemium sempervirens* diluted to 1/1000 of its standard tincture, the *Cephaelis ipecacuanha* diluted to 1/1000 of its standard tincture, the Phosphorus diluted to 1/100000 of its standard tincture, the Bryonia diluted to 1/100 of its standard tincture and the *Eupatorium perfoliatum* diluted to 1/10 of its standard tincture is present in two to four times the amount of any of the Cepa, the Euphrasia, the Belladonna, and the Mercurius solubilis.

3. The method of claim 1, wherein the medicament further comprises a combination including the *Aconitum napellus* diluted to 1/1000 of its standard tincture, the *Gelsemium sempervirens* diluted to 1/1000 of its standard tincture, the *Cephaelis ipecacuanha* diluted to 1/1000 of its standard tincture, the Phosphorus diluted to 1/100000 of its standard tincture, the Bryonia diluted to 1/100 of its standard tincture and the *Eupatorium perfoliatum* diluted to 1/10 of its standard tincture in a weight or in a volume of 4.0-4.5 g per 10 g of the medicament or 4.0-4.5 ml per 10 ml of the medicament, and the Cepa, the Euphrasia, the Belladonna and the Mercurius solubilis each in a weight or in a volume of 1.2-1.6 g per 10 g of the medicament or 1.2-1.6 ml per 10 ml of the medicament.

4. The method of claim 1, wherein the medicament is in a liquid form.

5. The method of claim 4, wherein the medicament is in an alcoholic solution.

6. The method of claim 1, wherein a combination including the *Aconitum napellus* diluted to 1/1000 of its standard tincture, the *Gelsemium sempervirens* diluted to 1/1000 of its standard tincture, the *Cephaelis ipecacuanha* diluted to 1/1000 of its standard tincture, the Phosphorus diluted to 1/100000 of its standard tincture, the Bryonia diluted to 1/100 of its standard tincture and the *Eupatorium perfoliatum* diluted to 1/10 of its standard tincture is present in a larger amount than each of the Cepa, the Euphrasia, the Belladonna and the Mercurius solubilis.

7. The method of claim 1, further comprising, alleviating symptoms of the herpes labialis and/or herpes genitalis and/or reducing an occurrence of relapses of the herpes labialis and/or herpes genitalis by administering the medicament to the patient.

8. A method, for reducing a course of herpes labialis and/or herpes genitalis comprising administering a medicament to a patient suffering from herpes labialis and/or herpes genitalis, the medicament comprising:

a combination including *Aconitum napellus* diluted to $1/10^3$ of its standard tincture, *Gelsemium sempervirens* diluted to $1/10^3$ of its standard tincture, *Cephaelis ipecacuanha* diluted to $1/10^3$ of its standard tincture, Phosphorus diluted to $1/10^5$ of its standard tincture, Bryonia diluted to $1/10^2$ of its standard tincture, *Eupatorium perfoliatum* diluted to $1/10$ of its standard tincture, wherein the combination is provided in a weight range of 4.0 to 4.5 g per 10 g of medicament;

Cepa diluted to $1/10^{12}$, wherein the amount of Cepa is provided in a weight range of 1.2 to 1.6 g per 10 g of medicament;

Euphrasia diluted to $1/10^{12}$, wherein the amount of Euphrasia is provided in a weight range of 1.2 to 1.6 g per 10 g of medicament;

Belladonna diluted to $1/10^{15}$, wherein the amount of Belladonna is provided in a weight range of 1.2 to 1.6 g per 10 g of medicament; and Mercurius solubilis diluted to $1/10^{12}$, wherein the amount of Mercurius solubilis is provided in a weight range of 1.2 to 1.6 g per 10 g of medicament.

9. A method, for
preparing a medicament to reduce a course of herpes labialis and/or herpes genitalis comprising:

combining *Aconitum napellus* diluted to $1/10^3$ of its standard tincture, *Gelsemium sempervirens* diluted to $1/10^3$ of its standard tincture, *Cephaelis ipecacuanha* diluted to $1/10^3$ of its standard tincture, Phosphorus diluted to $1/10^5$ of its standard tincture, Bryonia diluted to $1/10^2$ of its standard tincture, and *Eupatorium perfoliatum* diluted to $1/10$ of its standard tincture, wherein the combination is in a volume range of 4.0 to 4.5 ml per 10 ml of the medicament;

further combining Cepa diluted to $1/10^{12}$, wherein the amount of Cepa is provided in a volume range of 1.2 to 1.6 ml per 10 ml of the medicament;

further combining Euphrasia diluted to $1/10^{12}$, wherein the amount of Euphrasia is provided in a volume range of 1.2 to 1.6 ml per 10 g ml of the medicament;

further combining Belladonna diluted to $1/10^{15}$, wherein the amount of Belladonna is provided in a volume range of 1.2 to 1.6 ml per 10 ml of the medicament; and further combining Mercurius solubilis diluted to $1/10^{12}$, wherein the amount of Mercurius solubilis is provided in a volume range of 1.2 to 1.6 ml per 10 ml of the medicament.

10. The method of claim 9, further comprising, administering the medicament to a patient suffering from herpes labialis and/or herpes genitalis.

11. The method of claim 9, wherein the medicament is a drug or food supplement.

* * * * *

UNITED STATES PATENT AND TRADEMARK OFFICE
CERTIFICATE OF CORRECTION

| | | |
|---|---|---|
| PATENT NO. | : 8,043,634 B2 | Page 1 of 1 |
| APPLICATION NO. | : 12/345317 | |
| DATED | : October 25, 2011 | |
| INVENTOR(S) | : Klaus Huber | |

It is certified that error appears in the above-identified patent and that said Letters Patent is hereby corrected as shown below:

ON THE TITLE PAGE:

In Item (30) Foreign Application Priority Data:

Replace "20 2006 006 962 U" with "20 2006 004 962 U".

IN THE CLAIMS:

In Column 4 at line 65, Claim 1, replace "compromising" with "comprising".
In Column 4 at line 65, Claim 1, insert the word --medicament-- between "a" and "with".
In Column 5 at line 7, Claim 1, replace "cepa" with "Cepa,".
In Column 5 at line 7, Claim 1, replace "belladonna" with "Belladonna,".
In Column 6 at line 39, Claim 9, remove "g" between "10" and "ml".

Signed and Sealed this
Seventh Day of February, 2012

David J. Kappos
*Director of the United States Patent and Trademark Office*